US010206824B2

United States Patent
Bonelli

(10) Patent No.: US 10,206,824 B2
(45) Date of Patent: Feb. 19, 2019

(54) EXTENSIBLE LAMINAR MATERIAL, IN PARTICULAR FOR SANITARY ARTICLES, AND RELATIVE MANUFACTURING METHOD

(71) Applicant: Fameccanica.Data S.p.A., Pescara (IT)

(72) Inventor: Guido Bonelli, Pescara (IT)

(73) Assignee: FAMECCANICA.DATA S.P.A., Pescara (IT)

( * ) Notice: Subject to any disclaimer, the term of this patent is extended or adjusted under 35 U.S.C. 154(b) by 0 days.

(21) Appl. No.: 15/445,627

(22) Filed: Feb. 28, 2017

(65) Prior Publication Data
US 2017/0252229 A1    Sep. 7, 2017

(30) Foreign Application Priority Data
Mar. 1, 2016    (IT) .......................... 102016000021569

(51) Int. Cl.
*B32B 3/00*    (2006.01)
*A61F 13/49*    (2006.01)
(Continued)

(52) U.S. Cl.
CPC .. *A61F 13/49015* (2013.01); *A61F 13/15699* (2013.01); *A61F 13/15739* (2013.01); *A61F 13/15764* (2013.01); *A61F 13/4902* (2013.01); *A61F 13/496* (2013.01); *A61F 13/49014* (2013.01); *A61F 13/56* (2013.01); *A61F 13/58* (2013.01); *A61F 13/62* (2013.01); *A61F 13/625* (2013.01); *A61F 13/64* (2013.01); *B29C 65/08* (2013.01); *B29C 65/48* (2013.01); *B32B 3/02* (2013.01); *B32B 3/08* (2013.01); *B32B 3/26* (2013.01); *B32B 3/28* (2013.01); *B32B 5/022* (2013.01); *B32B 5/06* (2013.01);
(Continued)

(58) Field of Classification Search
CPC .......... A61F 13/15739; A61F 13/49015; A61F 13/15699; B32B 3/08; B32B 3/26; B32B 3/28; B32B 3/2555; B32B 5/022; B32B 5/06; B32B 5/142; B32B 7/045; B29C 65/08; B29C 65/48
See application file for complete search history.

(56) References Cited

U.S. PATENT DOCUMENTS

| | | |
|---|---|---|
| 4,568,344 A | 2/1986 | Suzuki et al. |
| 2011/0040273 A1 | 2/2011 | Sablone et al. |
| 2011/0046594 A1 | 2/2011 | Sablone |

OTHER PUBLICATIONS

Italian Search Report dated Nov. 18, 2016 for Application No. UB20161212.

(Continued)

*Primary Examiner* — Elizabeth E Mulvaney
(74) *Attorney, Agent, or Firm* — Patterson + Sheridan, LLP

(57) ABSTRACT

A transversely extensible elastic laminar web material comprising a first and a second web material each of which defines a first and a second distal region adjacent to corresponding longitudinal side edges and a central region between the aforesaid distal regions, at least one web of elastomeric material applied to these central regions of the first and second web materials and a plurality of connection formations applied to at least one distal region of said first and second web materials and projecting from a respective longitudinal edge. In the transversely extensible elastic laminar web material, the elastomeric web material and the connection formations are interposed between said first and second web materials and are joined thereto by mechanical welds.

8 Claims, 12 Drawing Sheets

(51) Int. Cl.
*A61F 13/15* (2006.01)
*A61F 13/496* (2006.01)
*A61F 13/62* (2006.01)
*B29C 65/08* (2006.01)
*B29C 65/48* (2006.01)
*A61F 13/56* (2006.01)
*A61F 13/58* (2006.01)
*A61F 13/64* (2006.01)
*B32B 5/02* (2006.01)
*B32B 5/06* (2006.01)
*B32B 5/14* (2006.01)
*B32B 7/04* (2006.01)
*B32B 25/10* (2006.01)
*B32B 27/12* (2006.01)
*B32B 3/02* (2006.01)
*B32B 3/08* (2006.01)
*B32B 3/26* (2006.01)
*B32B 3/28* (2006.01)
*B29L 31/48* (2006.01)

(52) U.S. Cl.
CPC ............ *B32B 5/142* (2013.01); *B32B 7/045* (2013.01); *B32B 25/10* (2013.01); *B32B 27/12* (2013.01); *A61F 2013/15869* (2013.01); *B29L 2031/4878* (2013.01); *B32B 2250/03* (2013.01); *B32B 2250/40* (2013.01); *B32B 2307/51* (2013.01); *B32B 2555/02* (2013.01)

(56) References Cited

OTHER PUBLICATIONS

EPO Extended European Search Report dated Jul. 27, 2017 for European Application No. 17158307.3.

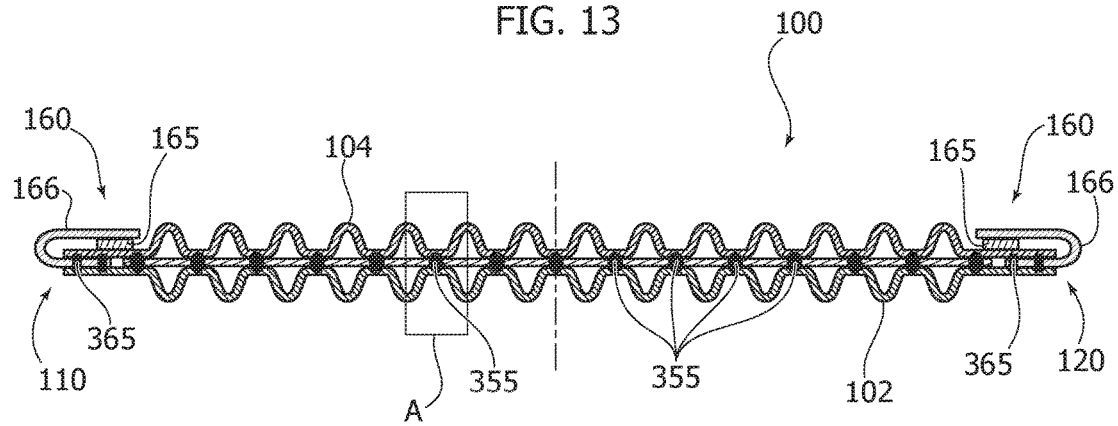
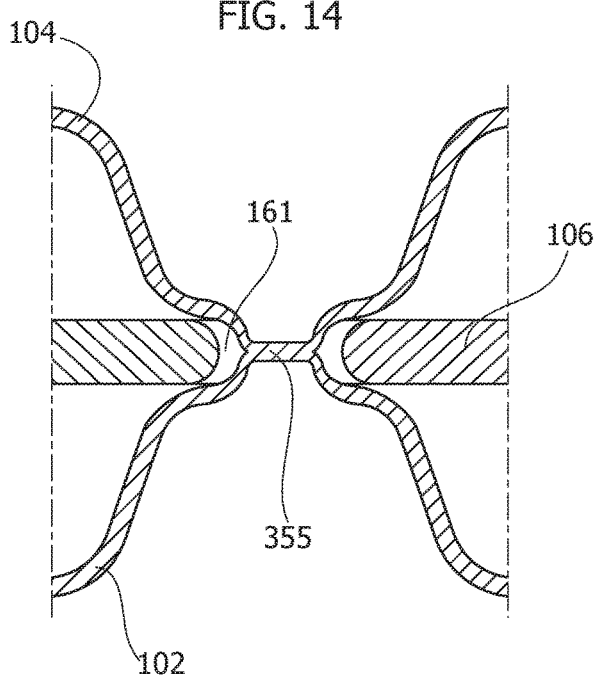

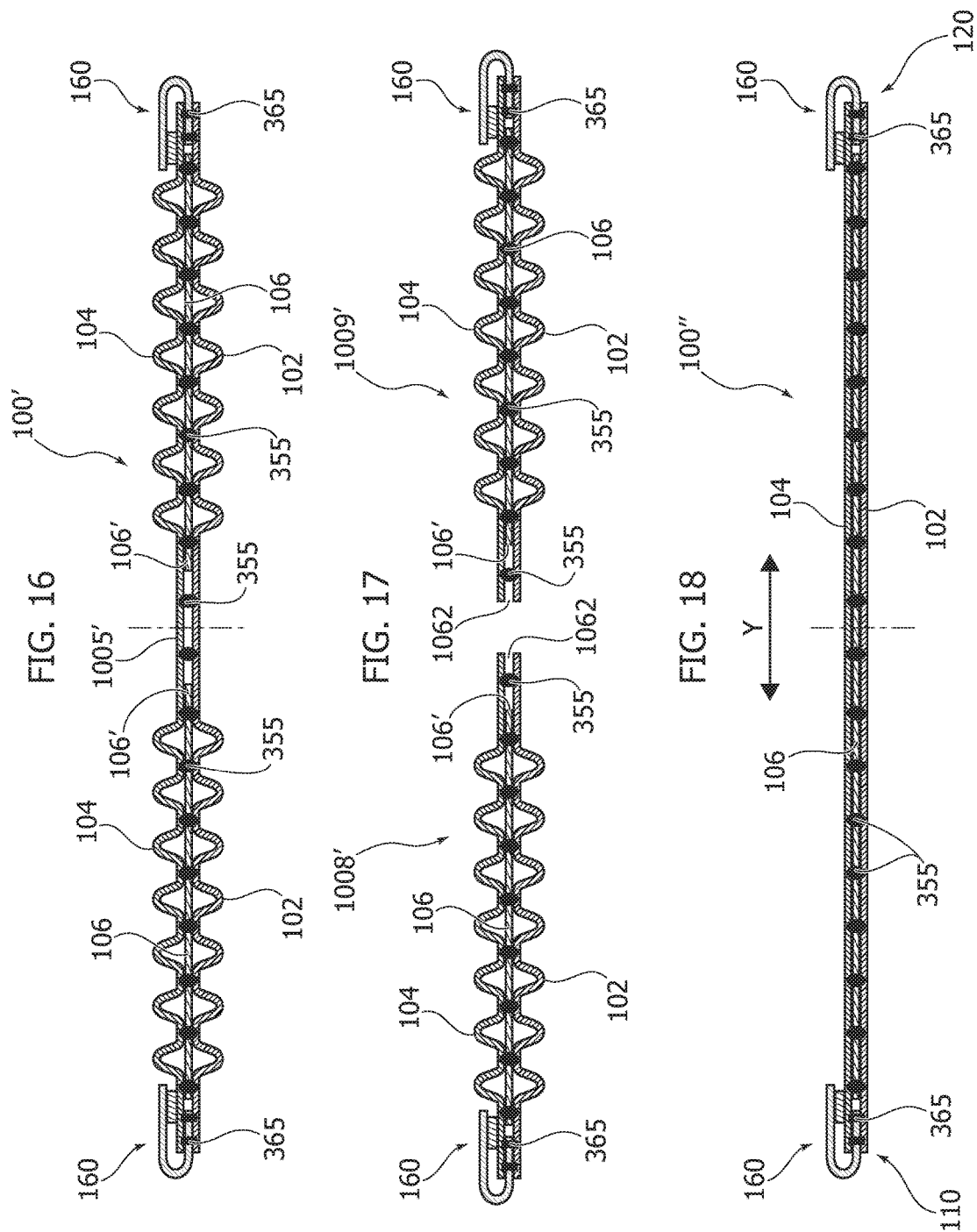

EXTENSIBLE LAMINAR MATERIAL, IN PARTICULAR FOR SANITARY ARTICLES, AND RELATIVE MANUFACTURING METHOD

CROSS-REFERENCE TO RELATED APPLICATIONS

This application claims benefit of Italian patent application number 102016000021569, filed Mar. 1, 2016, which is herein incorporated by reference.

BACKGROUND OF THE INVENTION

Field of the Invention

The present invention relates to a method for producing a semi-finished web product comprising a transversely extensible elastic laminar web material provided with connection formations.

The present description has been developed with particular reference to the possible application of the transversely extensible elastic laminar web material in the production of disposable absorbent sanitary products in the form of wearable pants, such as, for example, diapers for children and/or absorbent sanitary articles for incontinent adults.

Description of Prior Art

For some time, absorbent sanitary articles wearable as pants have a configuration that comprises a rectangular-shaped central body or chassis that is capable of having a basin arrangement around the crotch region of the user and at least one pair of side panels, which extend on opposite sides of at least one of the ends, front or rear, of the article provided with connection or closing formations capable of joining together the front and rear ends of the chassis of the absorbent article around the user's waistline.

There are many patent documents that address the problem of producing suitable materials for the production of side panels capable of combining characteristics of elastic extensibility as well as breathability.

An important development in the production of these materials is outlined in the document TO2008A000325, owned by the applicant, in which the disclosures are provided to produce an extensible laminar material obtained by coupling together two sheets of non-woven fabric with an interposed layer of elastic material, using a combination of adhesive lines and welds.

In any case, any connection formations necessary for joining together the front and rear ends of the sanitary article must be applied on the material intended to be used to produce the side panels, thus giving it the characteristic underpants conformation.

As is known, the connection formations attached to the ends of the side panels, precisely due to the function that they perform—namely to maintain the absorbent article closed in its underpants conformation—are subject to very high stresses, which can easily lead to breakage of the joint between the material of the side panels and the connection formation itself.

To resolve this problem, the specialized manufacturers—many years ago—developed said connection formations with a Y-shape. These connection formations have a multi-layer structure, which allows them to trap the side panel material between two laminar elements provided with a generous layer of adhesive. An example of a Y-shaped connection formation advantageously used for producing disposable sanitary articles is described in U.S. Pat. No. 4,369,786 entitled "Refastenable adhesive closure for disposable diapers or briefs" owned by the Avery International Corporation, Pasadena, Calif.

These solutions, while having led to satisfactory results, present problems related precisely to the complexity of their structure and to the need to use large quantities of adhesive which, as is known, belongs to a category of very polluting materials that have a high environmental footprint (carbon footprint). In addition to the above, the complex structure of the Y-shaped connection formations is reflected in a high cost, which is transferred to the selling price of the sanitary article.

To the above, it should be added that to produce the elasticized side panels, the use of significant quantities of adhesive may also be necessary.

Accordingly, the current state-of-the-art in the production of sanitary articles with elasticized side panels provided with connection formations presents problems related to the complexity and to the massive use of adhesives that it entails.

SUMMARY OF THE INVENTION

The present invention aims to provide a transversely extensible elastic laminar web material provided with connection elements with a simple structure able to excellently satisfy the requirements of environmental sustainability—outlined above—and also the cost requirements.

According to the present invention, this object is achieved thanks to a transversely extensible elastic laminar web material for side panels comprising connection formations having the characteristics referred to specifically in the claims that follow.

The invention also relates to the corresponding manufacturing method.

The claims form an integral part of the technical disclosure provided here in relation to the invention.

BRIEF DESCRIPTION OF THE DRAWINGS

The invention will now be described, purely by way of non-limiting example, with reference to the attached drawings, wherein:

FIG. 13 illustrates the structure of the material subject of the present invention according to the cross-section along the line XIV-XIV of FIG. 3.

FIG. 14 is an enlarged detail of FIG. 13.

FIGS. 16, 17 and 18 illustrate the structures of the material subject of the present invention according to further preferred embodiments.

In the following description, identical or similar components, or that perform the same function will be identified with the same reference numeral.

It is also appreciated that the drawings are schematic, are not to scale and the size ratios are not respected.

DETAILED DESCRIPTION

In the following description, various specific details are illustrated aimed at a thorough understanding of the embodiments. The embodiments can be implemented without one or more of the specific details, or with other methods, components, materials, etc. In other cases, known structures, materials or operations are not shown or described in detail to avoid obscuring various aspects of the embodiments.

The reference to "an embodiment" in the context of this description indicates that a particular configuration, structure or characteristic described in relation to the embodiment is included in at least one embodiment. Therefore, phrases such as "in an embodiment", possibly present in different places of this description do not necessarily refer to the same embodiment. Moreover, particular configurations, structures or characteristics can be combined in any convenient way in one or more embodiments.

The references used here are only for convenience and do not therefore define the field of protection or the scope of the embodiments.

The following clarifies the meaning of some terms that will be encountered in the rest of the discussion:

the term "elastic" or "elastomeric" defines the properties that a material possesses to resume its original shape and size once it is no longer stressed by the force that caused it to deform.

Typically, the term identifies a material that can be deformed by at least 25% of its original dimension at rest (or rather, stress-free) and that, once the force causing the deformation is removed, is able to recover at least 10% of the deformation. Generally, it is preferred that the elastic or elastomeric material is able to deform (or extend or stretch) by at least 100% and even more preferably by 300% with respect to its resting dimensions (relaxed) and is able to recover, once the elongation force (or deformation) is removed, at least 50% of its elongation;

the term "web" identifies a strip of flexible material that has much larger dimensions of length and width than the thickness. The web materials are typically supplied in rolls (or reels). Examples of web materials are non-woven fabric or elastomeric material films; and the terms "front" and "rear" are only used to distinguish between the two ends of an absorbent sanitary article and therefore do not have specific importance regarding the manner in which the aforesaid article is finally worn.

Figure 1:
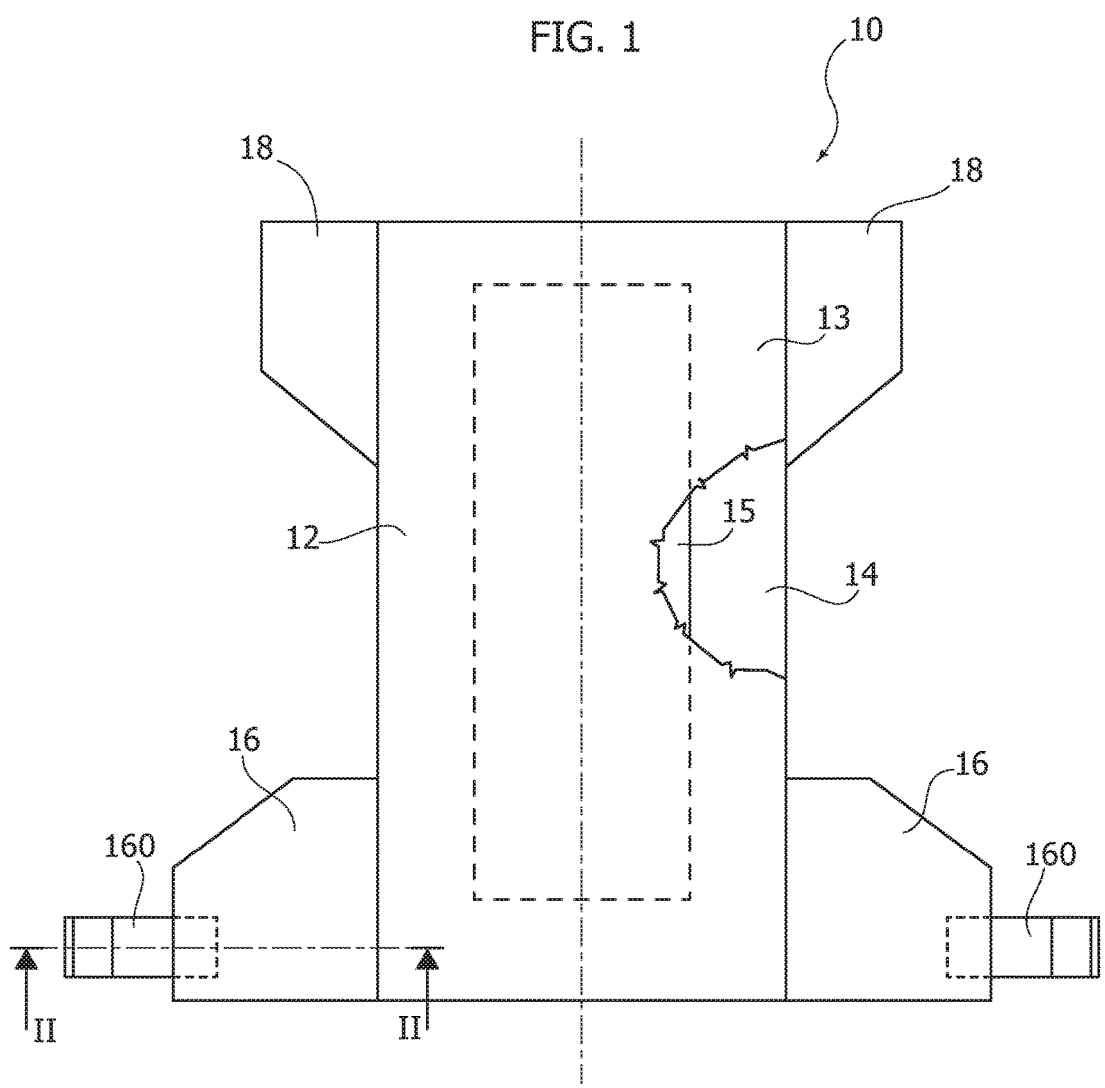
FIG. 1 is a general schematic view of a sanitary article, shown in an extended position, producible with the use of an extensible laminar material of the type described herein.

In FIG. 1, the reference number 10 indicates, in its entirety, a sanitary product wearable as pants, here illustrated in a flat extended position. It is, in the example illustrated here, a conventional-type absorbent sanitary article, commonly known as pant diaper for children or incontinence pads for incontinent adults, intended to be sold open and to be closed as pants after being placed on the wearer's body. The solution described here is, in any case, also applicable to the articles currently known as "reclosable training pants" intended to be sold already closed in their underpants configuration, ready to be worn by the user, but provided with connection formations that can be easily opened and, if necessary, also closed.

The product 10 illustrated here comprises a central body 12 intended to be applied around the user's groin region in a general U-shaped conformation.

The central body or chassis 12 has a structure in which the following are usually recognizable (in addition to various other accessory elements):

a top layer or "topsheet" 13 permeable to body fluids, intended to face towards the user's body;

a lower layer or "backsheet" 14 impermeable to body fluids, intended to face outwards, i.e. in the opposite position with respect to the user's body; and an absorbent core 15, interposed between the topsheet 13 and the backsheet 14.

A pair of front side panels 18 and a pair of rear side panels 16 are typically present at the front and rear ends of the central body 12.

In the preferred embodiment illustrated in FIG. 1, the rear side panels 16 are typically elastic and each of them is provided with a proximal edge 1602 connected to the central body 12, and a distal edge 1601 that typically has a connection formation 160, which allows the two front and rear ends of the central body 12 to be joined together, giving it the characteristic underpants conformation.

The connection formations 160 can be created in various forms and with different combinations of materials, which can give rise to various solutions known in the art.

Typically, the various connection formations 160 available in the market, are distinguished from each other by the closing means 165, which can be an adhesive element or a component with micro-hooks, and by the supporting element 166, which can be produced with the most varied range of materials, which, in turn, can be either elastic or non-elastic.

Figure 2:
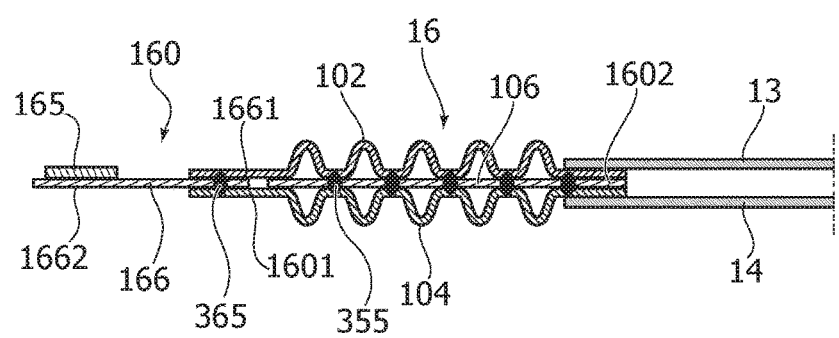
FIG. 2, essentially similar to a cross-section along the line II-II of FIG. 1, represents an element produced with an extensible laminar material of the type described herein.

In the following description, for simplicity, reference will be made to the connection formations 160 that comprise closing means 165 with micro-hooks and non-elastic support elements 166. On the support element 166 of each connection formation 160, it is possible to identify a proximal region 1661 and a distal region 1662. As illustrated in FIG. 2, the proximal region 1661 is one that is typically connected to the distal region 1601 of the side panel 16, formed by the transversely extensible elastic laminar web material 100 subject of the present invention, while the distal region 1662 carries the closing means 165 on it.

Suitable materials for producing a connection formation 160 can be:

for the supporting material 166, a non-woven SMS fabric with polypropylene fibers and with a grammage of 50 g/m$^2$. A material with these characteristics is produced by DOUNOR SA, 30-32 Rue Vertuquet, 59960 Neuville-en-Ferrain, France, and is identified by the code: Hymel PPSM/50/E/O/S.

for the closing means 165, a material provided with hook elements, such as Microplast ITEM-no:85445 in polypropylene of 100 g/m$^2$, can be advantageously used, produced and marketed by GOTTLIEB BINDER GmbH u. Co KG, Bahnhofstrasse 19, D-71088 Holzgerlingen, Germany.

The supporting element 166 and the closing means 165 can be joined together using adhesive or even more advantageously with thermomechanical and/or ultrasonic welds. In the case of joining with glue, a suitable adhesive for this type of application can be the Full-Hook™ NW 1192 F, produced and marketed by H. B. Fuller http://www.hbfuller.com.

The embodiment illustrated here refers to a sanitary product in which the elasticized side panels 16 are only present at the rear end of the central body 12, while its front end is provided with two wings 18, which are typically made with a non-elastic material that contribute to confer the typical hourglass conformation to the article 10 (seen ideally in the open and extended position, as represented in FIG. 1).

The representation of FIG. 1 is schematic in nature and intends to highlight that the solution described herein can be applied to a wide variety of possible constructive types of absorbent sanitary articles 10.

For a more detailed description about the additional characteristics and materials that can typically be included in the article 10, please refer to the wide range of existing literature on the subject.

Figure 10:
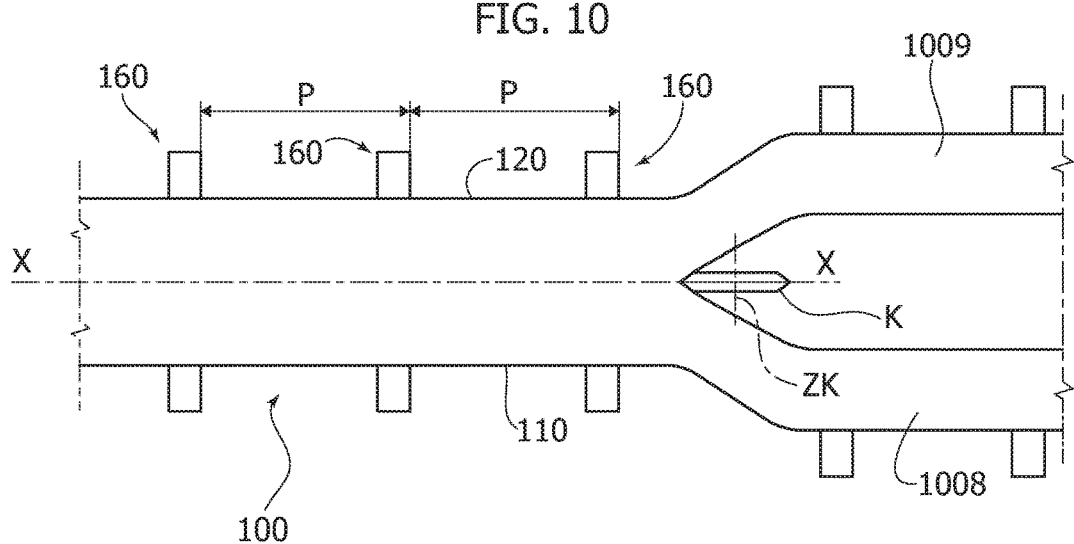
FIGS. 10 to 12 represent possible embodiments of the material subject of the present invention.
Figure 11:
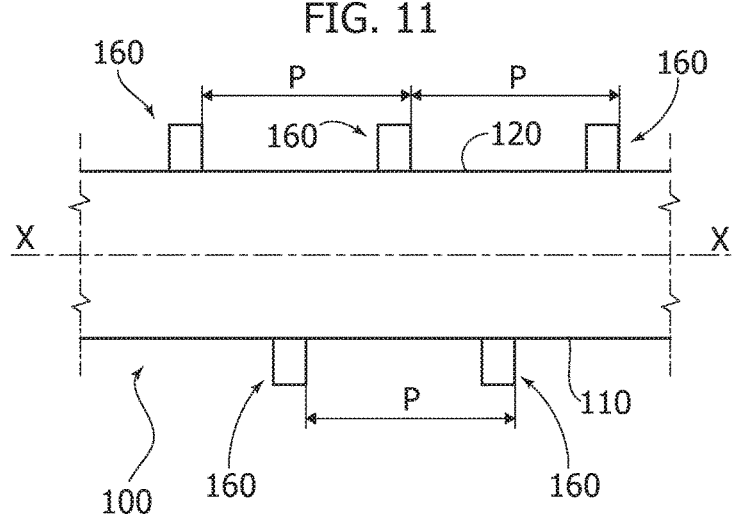

The transversely extensible elastic laminar web material 100, illustrated, for example, in FIGS. 10 and 11, defines a longitudinal axis X-X and a first and a second longitudinal edge 110 and 120, parallel to it, from which the connection formations 160 protrude, and typically has a layered structure formed of a first web material 102 and a second web material 104—for example of non-woven fabric—between which a web of elastomeric material 106 is interposed.

Figure 7:
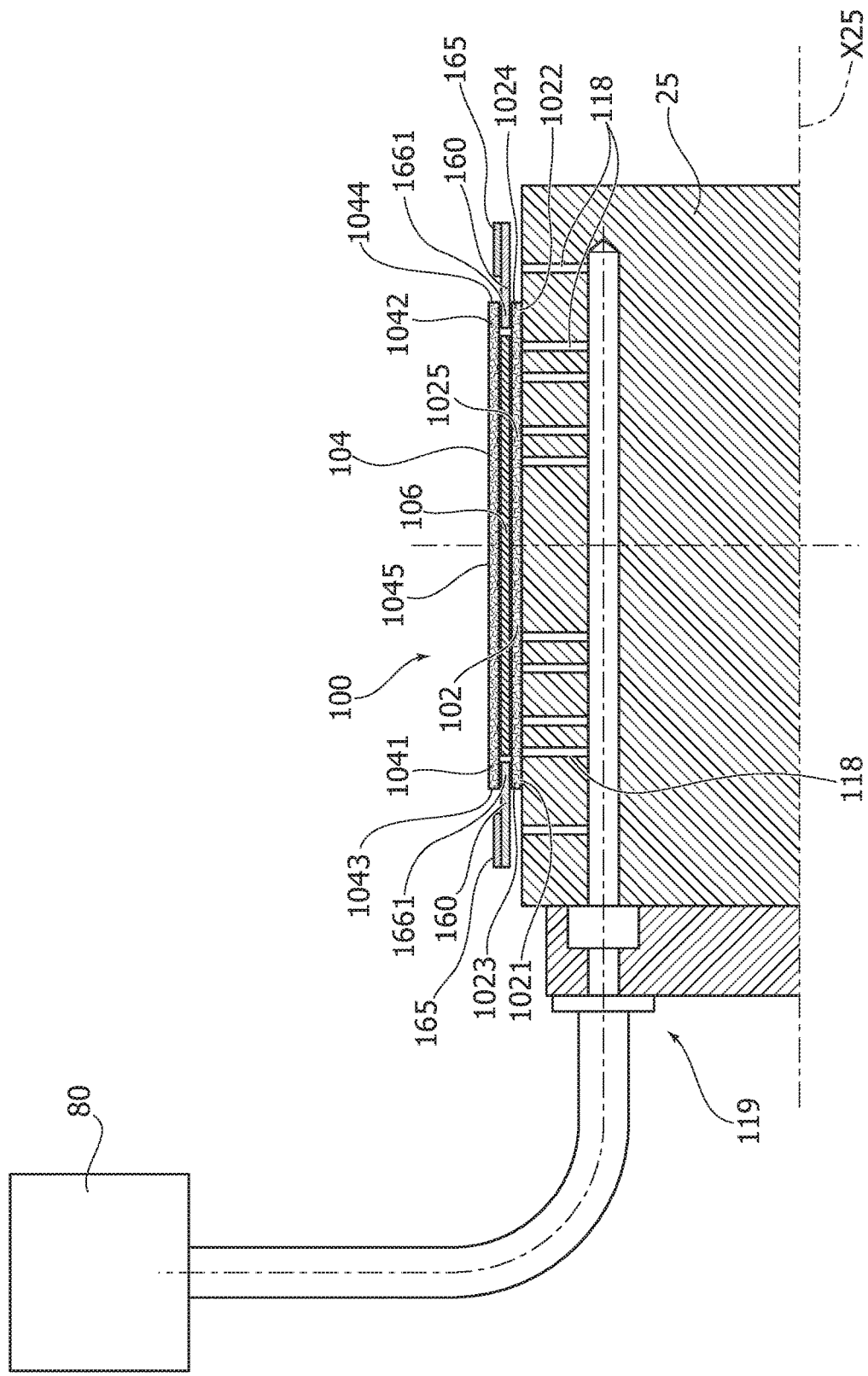

As shown, for example, in cross-section in FIG. 7, in the first web material 102, it is possible to identify a first distal region 1021 and a second distal region 1022, adjacent to the respective longitudinal side edges 1023, 1024, and a central region 1025 between said distal regions.

Similarly, in the second web material 104, it is possible to identify a first distal region 1041 and a second distal region 1042, adjacent to the respective longitudinal side edges 1043, 1044, and a central region 1045 between said distal regions.

Typically, the first and the second longitudinal edges 110 and 120 of the transversely extensible elastic laminar web material 100 are coincident with the respective first and second longitudinal edges 1023, 1024, 1043 and 1044 of the first and second web materials 102 and 104 that compose it.

To produce a transversely extensible elastic laminar material 100 provided with connection formations 160, the first and the second web materials 102 and 104 can be constituted of non-woven fabric having a grammage, for example, in the order of 10 g/m². A material with these characteristics is produced by Fibertex Nonwovens A/S, Svendborgvej 16, 9220 Aalborg, Denmark, and is marketed under the name Hydrofobic NW SMS spunbond XW 010 01 001 or FW 010 01 001. A web of elastomeric material 106 suitable for this particular application could be the film known as CEX802WR, produced and marketed by the TREDEGAR CORPORATION of Richmond, Va., USA.

It is evident that the reference to these specific materials is purely illustrative, and should not be construed in a sense limiting the scope of the present description.

It should be emphasized that the connotation "first" and "second" is used in the present description solely to distinguish between two elements or two characteristics of the same element and has not, therefore, specific importance with regard to the manner in which the product is finally produced.

Figure 3:
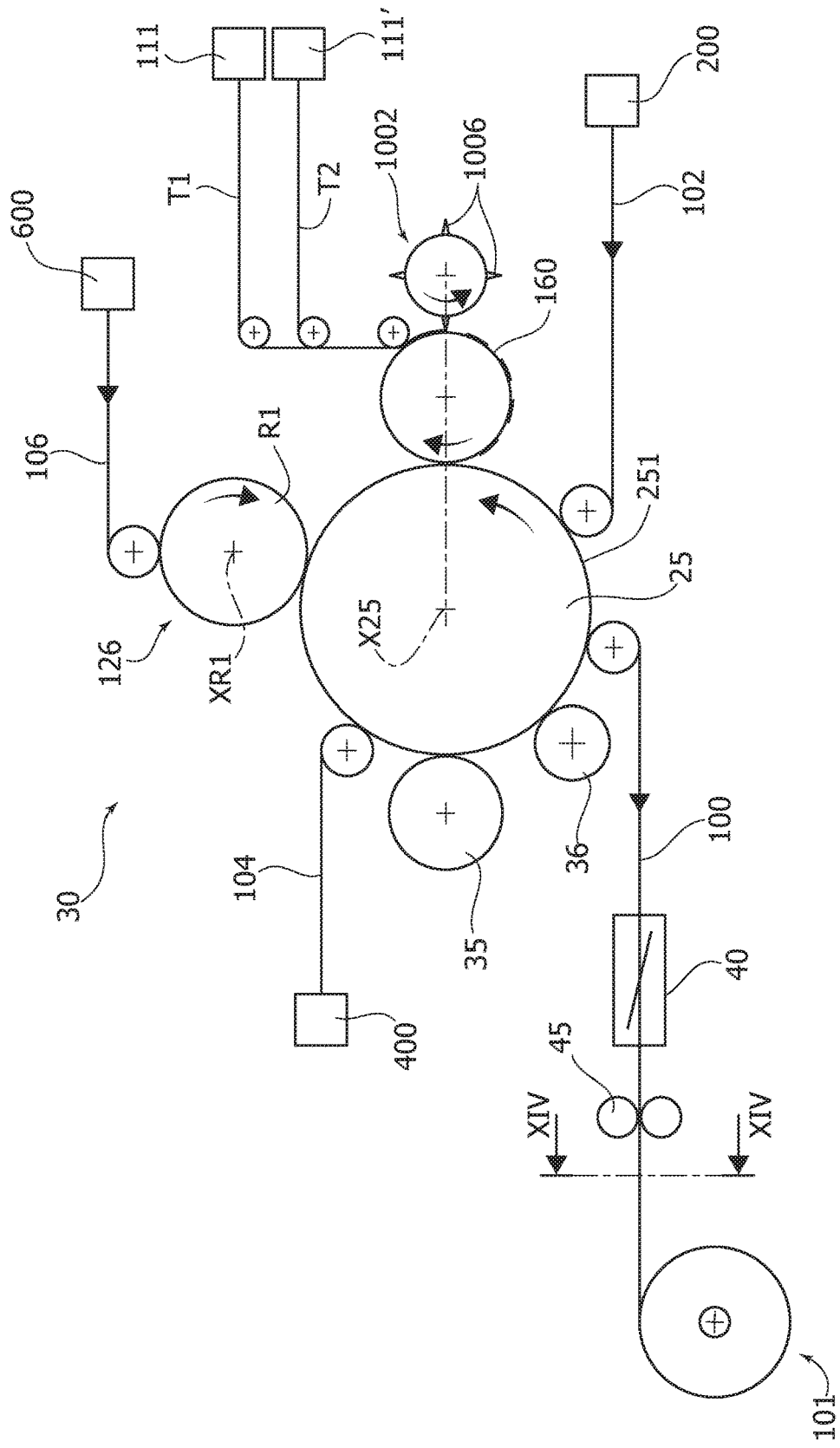
FIG. 3 is a schematic view of an apparatus for producing a transversely extensible laminar web material according to a preferred embodiment of the present invention.

FIG. 3 illustrates a side elevational view of an apparatus 30 according to a preferred embodiment for producing a transversely extensible elastic laminar web material 100 provided with connection formations 160, particularly suitable for use in producing the elasticized side panels 16.

Figure 4:
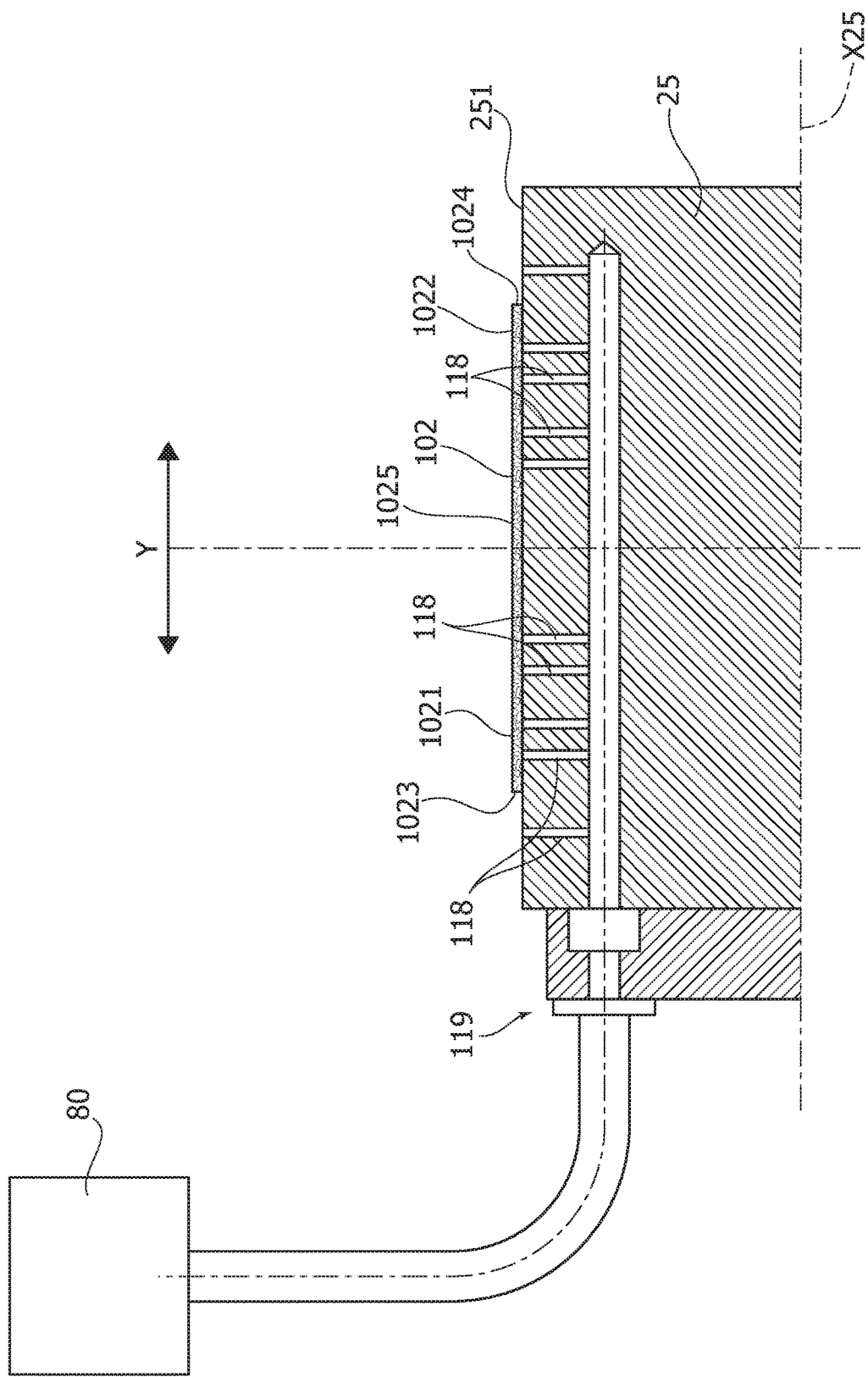
FIGS. 4 to 9 illustrate successive production steps of such a material.

With reference to FIGS. 3 and 4, the production apparatus 30 is typically fed with a first web material 102 supplied by an unwinding device of the rolls (or reels) of web materials 200, well known in the art.

The web material 102 is typically placed on the outer surface 251 of a cylindrical roller 25, rotating around its own horizontal axis X25.

In the preferred embodiment, the web material 102 can be retained and maintained in an extended condition on the outer surface 251 of the roller 25 thanks to a plurality of holes 118 and appropriate vacuum distribution means 119, which allow the connection of the outer surface 251 of the roller 25 with a sub-atmospheric pressure source 80, and which grasp the distal regions 1021 and 1022 of the first web material 102, preventing it from shrinking transversely; the usefulness of retaining the material at the regions adjacent to the longitudinal side edges of the web material 102 will become clear in the following description.

In the art, various alternative devices to the vacuum are available for the transverse gripping of web materials, in fact, this result can be achieved in different ways: for example, anchoring of the first web material 102 onto the outer surface of the roller 25 with counter-rollers, or with retaining belts or, alternatively, producing side zones of the outer surface of the roller 25 with a high coefficient of friction, as described in the document EP 1 982 823 A2, by the same applicant, entitled "method and device for treating web material".

Subsequently, in the preferred embodiment illustrated in FIG. 5, the connection formations 160 are typically applied, with the respective proximal regions 1661 overlapping with the distal regions 1021 and 1022 of the first web material 102 and with the distal regions 1662 that carry the relative closing means 165 projecting from the longitudinal edges 1023 and 1024 of the web 102.

The operation of applying the connection formations 160 onto the first web material 102 can be implemented by means of an appropriate application device 1002, well-known in the art, such as the cutting and pitch application device described in EP 1 864 768 A1 entitled "A cutting device, for example for producing sanitary products, and relative actuating methods" owned by the applicant. Each connection formation 160 is typically placed onto the web material 102 with a predefined and constant application pitch P so that each connection formation 160 is equidistant from the connection formation 160 that precedes it and the one that follows it, applied on the same distal region 1021, 1022 of the web 102.

A connection formation 160 can also be formed by a plurality of connection formations 160', suitably grouped, as represented in FIG. 13; in this case as well, each multiple connection formation 160 is typically placed on the web material 102 with a predefined and constant application pitch P in such a way that each multiple connection formation 160 is equidistant from the multiple formation connection 160 that precedes it and from the multiple connection formation 160 that follows it, applied on the same distal region 1021, 1022 of the web 102.

Figure 12:
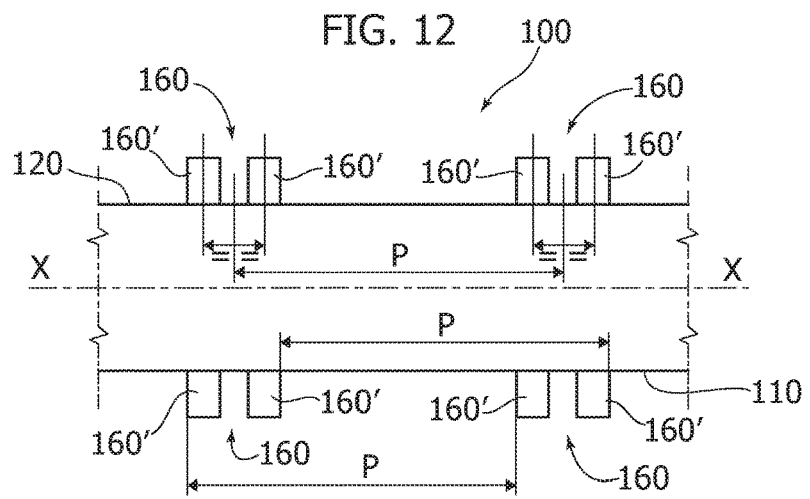

The connection formations 160 can be applied on the web material 100 so as to protrude from only one edge or, more preferably, from both its longitudinal edges 110 and 120, as shown for example in FIG. 7. In the latter case, the connection formations 160 can be juxtaposed to each other, as shown in FIGS. 10 and 12, or offset, as shown in FIG. 11.

In the remainder of the document, without diminishing the generality in the discussion, reference will be made to the production of a semi-finished web product 100 provided with connection formations 160 that protrude from both its longitudinal edges 110 and 120, and juxtaposed to each other, as illustrated in FIG. 10. Such a transversely extensible elastic laminar web material 100 produced in this way can be left intact, or, typically, can be cut with a knife K, in turn, along its longitudinal axis X-X, so as to form two webs of material 1008 and 1009 specular to each other, which are typically intended to be further processed so as to form the elastic side panels 16 to be applied on opposite longitudinal edges of the central body 12 of a sanitary product 10.

In the preferred embodiment, the application unit 1002 of the connection formations 160 is typically fed with two web materials T1 and T2 that are segmented by the knives 1006, which is equipped in such a way so as to obtain the connection formations 160 from these continuous webs.

The web materials T1 and T2 are typically supplied by unwinding apparatuses of rolls (or reels) of web material 111 and 111', also well-known in the art.

Figure 5:
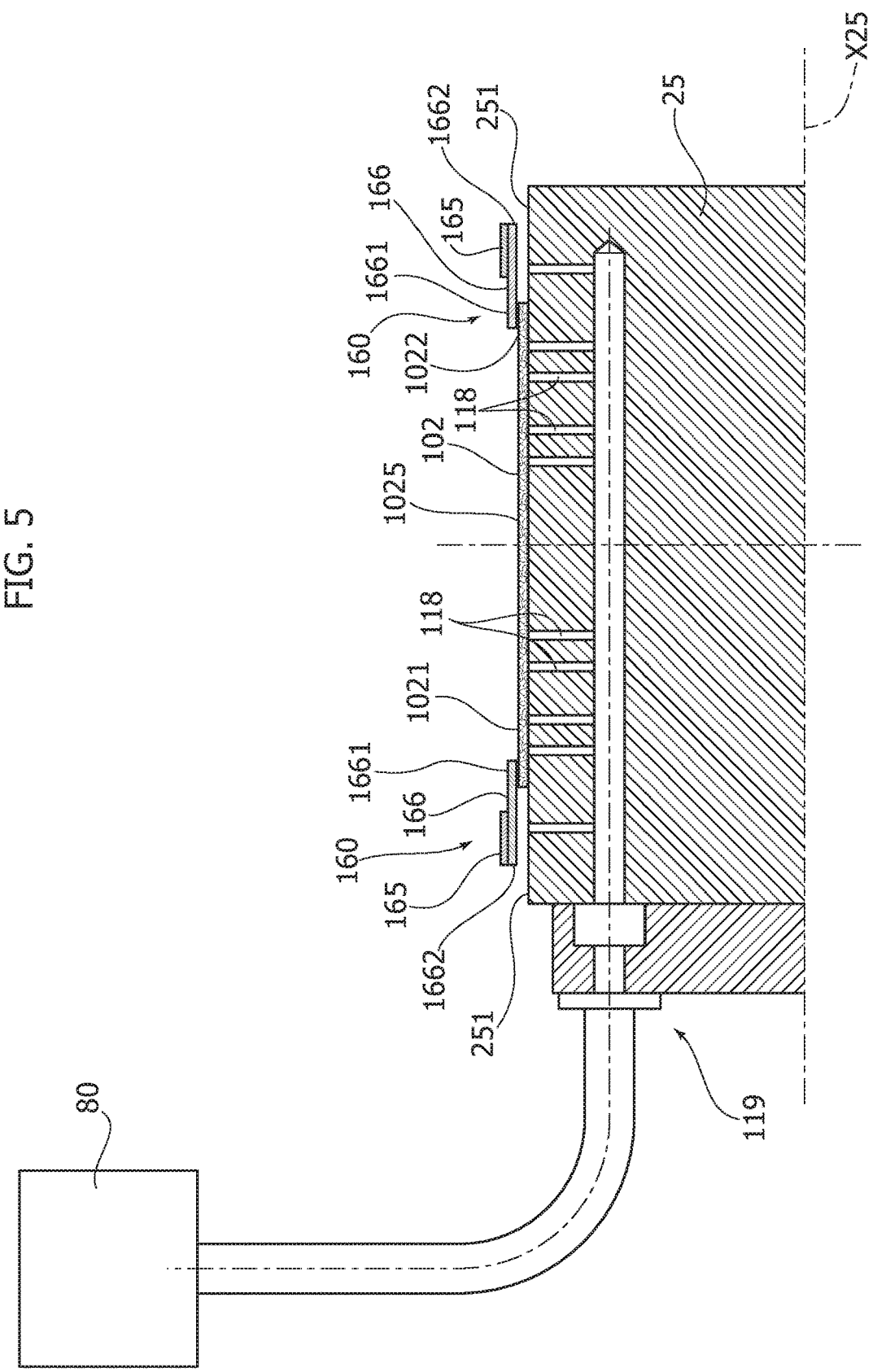

The connection formations 160, once placed on the distal regions 1021 and 1022, adjacent to the longitudinal side edges of the web 102, are typically held in position on the roller 25 during the implementation of the subsequent steps of the method, by means of suitable retaining means, which in the preferred embodiment, can be suction holes 118 connected to the sub-atmospheric pressure source 80 with appropriate vacuum distribution means 119 as shown in FIG. 5.

To maintain the connection formations 160 in the correct position on the first web material 102 during the various steps of the manufacturing method of the web material 100, it is also possible to produce technical joints using modest quantities of adhesive (in the order of 1-3 g/m$^2$), capable of retaining the connection formations 160 on the web material 102 during the construction of the web material 100 but which, however, because of the modest amount of adhesive used, are not sufficient to ensure an adequate anchorage of the connection formations 160 on the material 100 when it is used as a side panel of a sanitary article 10.

Adhesives able to produce this function of technical joints are known, for example, in the production of the Saveré company of Milan.

Figure 6:
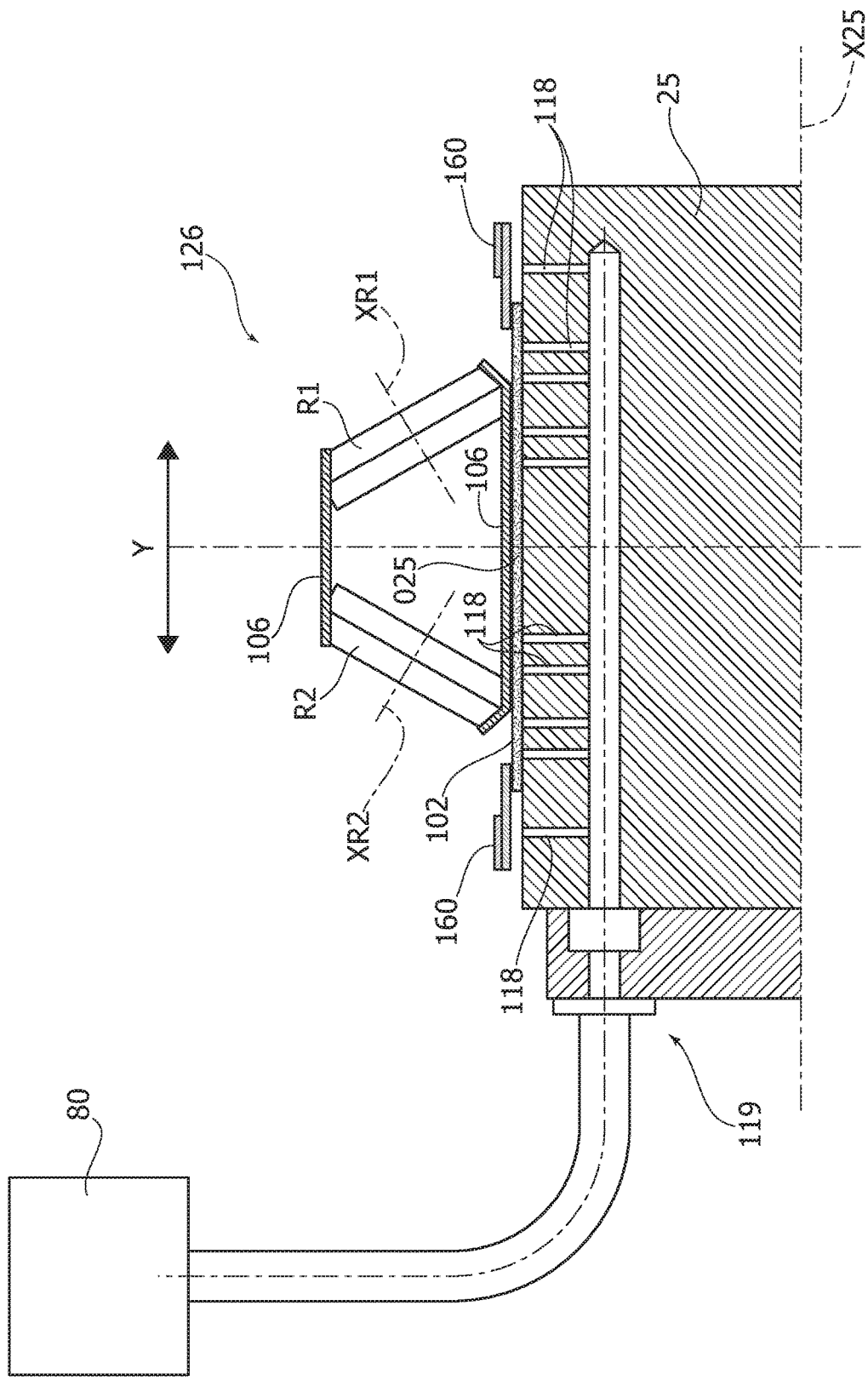

After having placed the connection formations 160 on the web 102 at its central region 1025, it is typically coupled to a web of elastomeric material 106, provided from an unwinding device of rolls (or reels) of elastomeric web material 600 well-known in the art, typically in an extended condition in the transverse direction Y, shown in FIG. 6.

The web of elastomeric material 106 is also held in position and made to adhere to the first web material 102 with suitable anchoring means, which in the preferred embodiment can be the same suction holes 118 connected to the sub-atmospheric pressure source 80 with the vacuum distribution means 119, which can act on the elastomeric web material 106 by exploiting the permeability to gases of the first web material 102, which is typically a sheet of non-woven fabric and, therefore, breathable per se.

From the above, it is apparent why in the preferred embodiment it is necessary to keep the distal regions 1021 and 1022 of the first web material 102 blocked. In fact, if the first web material 102 was not retained at the side edges, it would not be able to resist the recall action of the elastomeric web material 106 and would, therefore, contract, curling transversely on itself.

The web of elastomeric material 106 is applied on the first web material 102 in the extended state in the transverse direction Y, i.e. in other words in a transverse direction relative to the longitudinal direction of the laminar web material 100.

In a preferred embodiment, the degree of deformation (or extension) imparted to the web of elastomeric material 106 is in the order of 200%. This means that the web of elastomeric material 106 is applied onto the first web material 102 (making it adhere at its lateral margin due to the suction holes 118), keeping it stretched transversely at a width essentially equal to three times the width that the web of elastomeric material 106 would present under resting conditions, i.e. in the absence of extension stress in the transverse direction.

In the preferred embodiment, as illustrated in FIG. 6, the transverse extension of the elastomeric web material 106 is obtained by a spreading-apart device 126 comprising two wheels R1, R2 with respective axes XR1, XR2, incident and oblique to each other.

The web of elastomeric material 106 is fed to the wheels R1, R2, where, due to the oblique arrangement of the respective rotation axes, the peripheries of the two wheels are closer together.

To allow the operation of transverse stretching of the web of elastomeric material, it is typically retained on the outer surface of the wheels R1 and R2 with appropriate retaining means, which may be, for example, a vacuum or retaining belts or, alternatively, side zones of the outer surface of the wheels R1 and R2 with a high coefficient of friction, or a combination thereof.

Due to the rotation of the wheels, the web of elastomeric material 106 is gradually carried to the area in which the peripheries of the wheels R1, R2, themselves are more distant from each other, obtaining the desired transversal deformation, and then proceeding to the application of the web of elastomeric material 106 on the layer 102 in this transversely extended condition.

A technique similar to the transverse extension of laminar materials is known in the art in various possible embodiments as shown, for example, in the document U.S. Pat. No. 5,308,345. This, therefore, means that a more detailed description of this solution in the context of the present application, is superfluous.

The anchoring action achieved by means of the vacuum of the suction holes 118 ensures that, even when disengaged from the transverse extension unit comprising the wheels R1 and R2, the layer of material 106 maintains the extended condition. As already said, the vacuum holes 118 retains the extensible sheet of material 106 adhering to the first web material 102 which, in turn, is also retained in position adherent to the outer surface of the roller 25 by the vacuum of the holes 118, so that—in spite of the action of elastic recall of the layer 106—the composite web formed by the first web material 102 and by the elastomeric web material 106 is maintained in its extended form and does not contract transversely.

At this point, in the preferred embodiment illustrated in FIGS. 3 and 7, the production apparatus 30 is typically fed with a second web material 104, which is also supplied by an unwinding device of rolls (or reels) of web material 400, well-known in the art. Typically, the second web material 104 is applied with its central region 1045 above the web of elastomeric material 106, and with the distal regions 1041 and 1042 overlapping the respective distal regions 1021 and 1022 of the first web material 102 and the proximal regions 1661 of the connection formations 160 in such a way as to have the longitudinal edges 1043 and 1044 coincident with the edges 1023 and 1024, respectively, so as to complete the sandwich structure of the laminar web material 100.

Subsequently, the aforesaid sandwich comprising the web of elastomeric material 106 and the plurality of connection formations 160 interposed between the first and the second web materials 102 and 104 is subjected to a welding treatment, which combines the first and the second web materials 102 and 104, the connection formations 160 and the web of elastomeric material 106 with a plurality of welds 355 and 365, which are typically produced by the welding devices 35 and 36. The welds 355 and 365 give coherence to the sandwich structure and prevent the resulting transversely extensible elastic laminar web material 100 being affected by a delamination phenomenon (i.e. detachment) of the various elements 102, 104, 106 and 160 that compose it, preferably without the aid of adhesives.

In the illustrated embodiment, ultrasonic welding devices can represent a preferred choice capable, however, of being replaced with equivalent techniques, such as heat-sealing or cold pressure welding.

In the preferred embodiment illustrated in FIG. 3, because of the different thicknesses and different types of materials to be welded, the welding treatment is typically implemented with more welding devices, which can be arranged adjacent to each other or in succession. Alternatively, the welding treatment could be implemented with just one welding unit, at the cost of a greater complexity of the possible welding device.

As can be seen from FIG. 3 that schematically illustrates the preferred embodiment, the welding devices 35 and 36 are arranged in succession, one after the other. The first welding device 35 (which is typically positioned upstream in the process, i.e. immediately after the lamination in the second web material 104) preferably produces the coupling of the sheet of extensible material 106 with the first and the second web materials 102 and 104 between which it is interposed, forming the junction points or welds 355, and can be constituted by at least one ultrasonic welding head. The second welding device 36, which is typically placed immediately after the first welding device 35, is responsible for forming the welds 365, which connect the connection formations 160 with the web materials 102 and 104 and which join together the distal regions 1021, 1022, 1041 and 1042 of the two web materials 102 and 104 in the sections between two successive connection formations 160.

Figure 9:
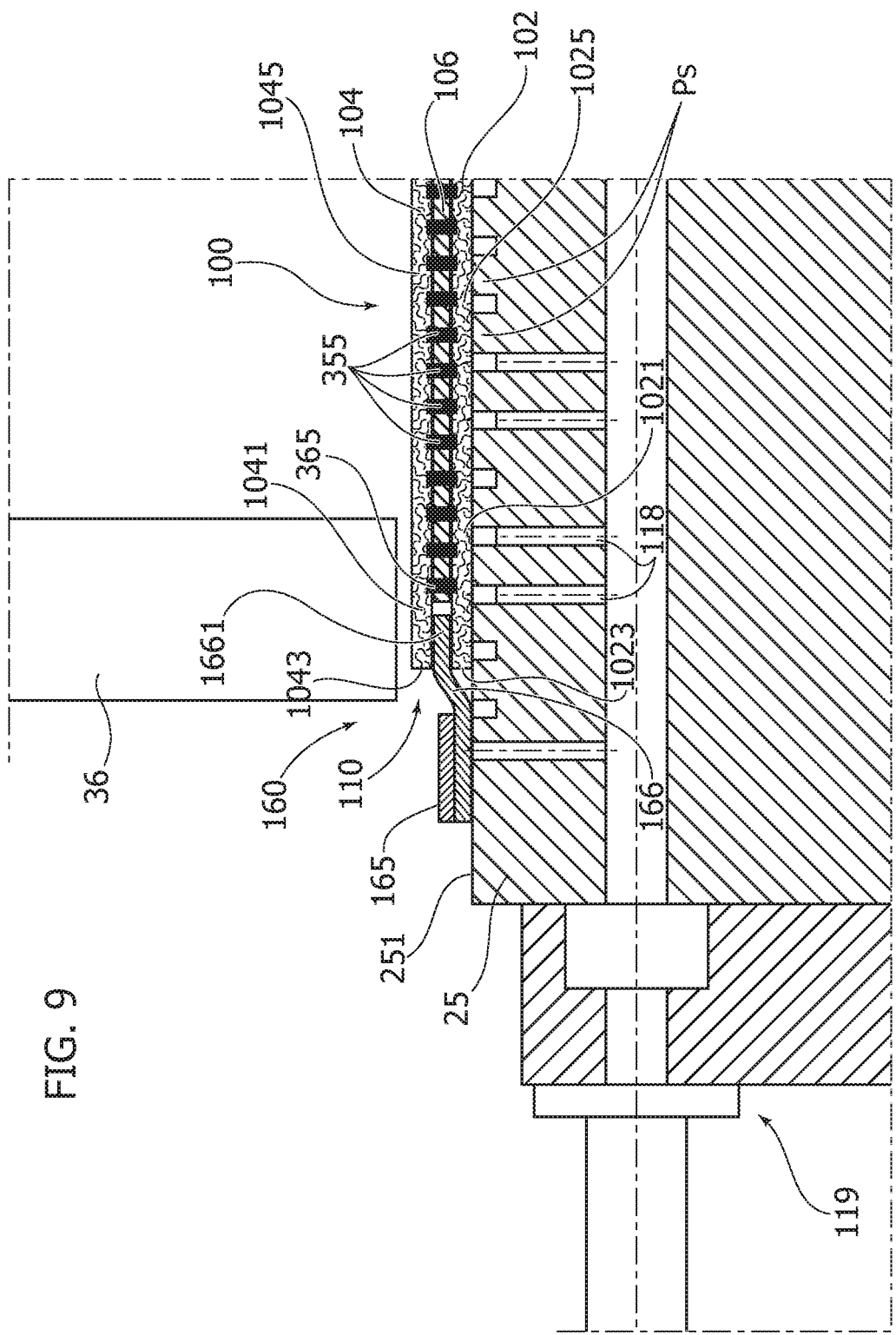

The second welding device 36 may comprise at least one ultrasonic welding head, although preferably, as can be seen from FIG. 9, the said second welding device 36 typically comprises two ultrasonic welding heads.

It is obvious that the arrangement illustrated in FIG. 3 is not binding and does not detract generality from the description. In fact, it could be possible to have the welding devices 35 and 36 in any other arrangement, i.e. the two welding units could be reversed or could be aligned.

Ultrasonic welding devices suitable for the applications described herein can be provided by Herrmann Ultraschalltechnik GmbH & Co. KG.—Descostrasse 3-9, 76307 Karlsbad—Germany. A device suitable for both welding processes is typically composed of an Ultrasonic Generator model DYNAMIC digital control 4000 CS, a titanium converter model CCS 20-S-IP50-L-I, a titanium Booster 20 KHz ratio 1:1.4 and a titanium Sonotrode 20 kHz$\lambda$=1/2, MS 85/45/16 Square.

In the preferred embodiment illustrated in FIG. 3 the welding treatment implemented by the first welding device 35, which produces the sandwich material 102, 104 and 106, can typically give it the characteristic of breathability, which is the ability of a typically laminar material to be permeable to gases (air and steam) so as to allow the user's skin to "breathe".

Therefore, in the preferred embodiment, while the first and the second web materials 102 and 104 are typically webs of non-woven fabric—breathable per se—the web of elastomeric material 106, which is typically a web of non-breathable material, during the welding step can be perforated and therefore can be made permeable to gaseous substances. This treatment is essentially similar to the formation of a pattern of openings 161 formed in the elastic material of the sandwich structure by means of appropriately-shaped protuberances of the welding pattern Ps, which is typically present on the outer surface 251 of the roller 25.

Typically, the weld 355 of the first and the second web materials 102, 104 and the hole 161 of the web of elastomeric material 106 are produced in a single step since the molecules of the material of the said web of elastomeric material 106 that are located at the protuberances of the pattern Ps when they are hit by the sonotrode due to the hammering action, migrate suddenly towards the edges of the protuberance of the said pattern Ps, leaving only the two web materials 102 and 104 to undergo the action of the ultrasonic welding device 35 which produces the weld 355, represented in detail in FIG. 14.

Figure 8:
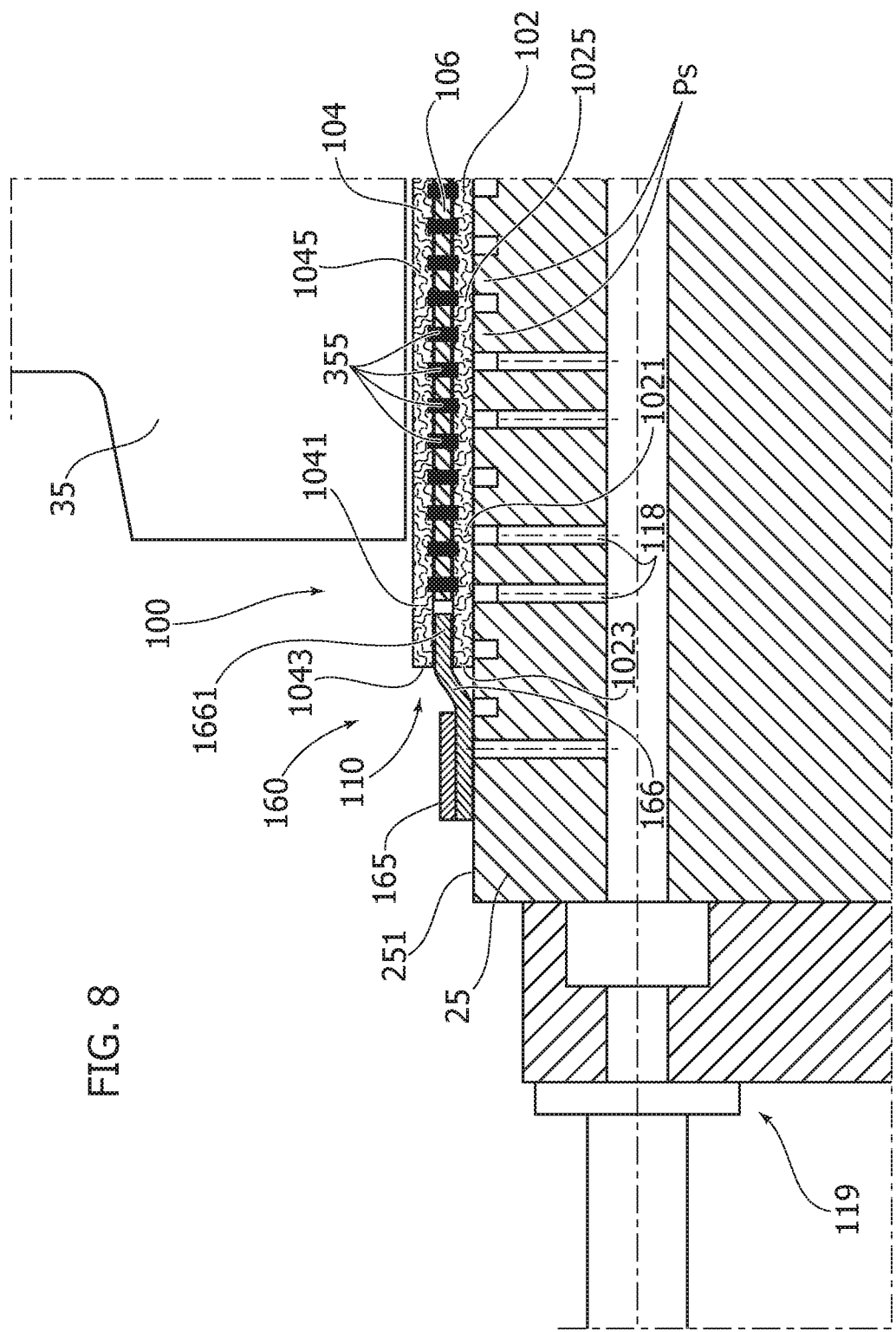

The view of FIG. 8 is intended to illustrate—in general terms—the various parts that come into play in the welding process implemented by the first welding device 35, in which the parts are shown spaced-apart for clarity.

FIG. 9 illustrates, instead, the various parts that come into play in the welding process implemented by the second welding device 36, and in this case as well, the aforesaid parts are shown spaced-apart for greater clarity.

The web 100, produced as such, as soon as it leaves the production machine 30 is typically made to flow through a folding device 40 of the connection formations 160, known in the art, which folds them on the web 100 itself around the respective longitudinal edges 110 and 120 according to a general V-shaped conformation. It is also possible to reinforce the binding of each connection formation 160 with the distal regions 1021, 1022, 1041 and 1042 of the web materials 102 and 104 through a compressing operation performed in a pressing station 45 located downstream of the folding device 40. The pressing station 45, also known in the art, is typically provided with a pair of contra-rotating rollers kept pressed against one another with suitable thrust means, such as pneumatic cylinders.

At the end of this treatment the web 100, completed in its sandwich structure formed by the web materials 102 and 104 with the web of elastomeric material 106 and the connection formations 160 interposed between said web materials 102 and 104, and optionally folded in a V-shape, can be sent directly to a production line of sanitary articles 10, or can be wound around reels which, in turn, can be used at a later time on these production lines.

Once freed from the constraints that prevent the contraction and after having folded the connection formations 160, the transversely extensible elastic laminar web material 100 assumes the transverse profile visible in the cross-section shown in FIG. 13, where it can be seen that in the transversely extensible elastic laminar web material 100, once the action of transverse stretching is removed, the web of elastomeric material 106 contracts itself to return to its original size (at rest), which causes the shrinking of the first and second web materials 102 and 104 forming transverse ripples on them in the areas in which they are not connected to each other and/or to the web of elastomeric material 106.

The transversely extensible elastic laminar web material 100 described herein is, therefore, elastically extensible in the transverse direction starting from the resting condition represented in FIG. 13 up to an extended condition essentially similar to that shown in FIG. 9 which, as already said, represents half of the second welding device 36 and in which the condition is clearly visible in which the web of elastomeric material 106 is interposed in the transversely extended sandwiched condition between the two web materials 102 and 104 maintained in their original flat condition.

Once laterally extended, up to reaching this condition of maximum extension, the transversely extensible elastic laminar web material 100 then demonstrates marked resistance against any further attempt to transversely extend, as any further extension would entail the need to also transversely deform the first and second web materials 102 and 104 which, by their nature, are essentially inextensible.

In a further embodiment, illustrated in FIGS. 16 and 17, it is advantageous to have a transversely extensible elastic laminar web material 100', which has the central region 1005' devoid of elastication, from which it is possible to produce two webs 1008' and 1009' by longitudinal cutting of the web 100', similarly to that shown in FIG. 10, from which the elastic side panels 16 can be obtained with non-elastic proximal regions 1602, resulting from the central region 1005' of the web 100', i.e. devoid of ripple characteristics of the elasticized parts, therefore easier to apply on the side edges of the central body 12 of the sanitary article 10, as represented in FIG. 2.

This characteristic can be achieved by cutting the web of elastomeric material 106 along its own longitudinal axis.

Figure 15:
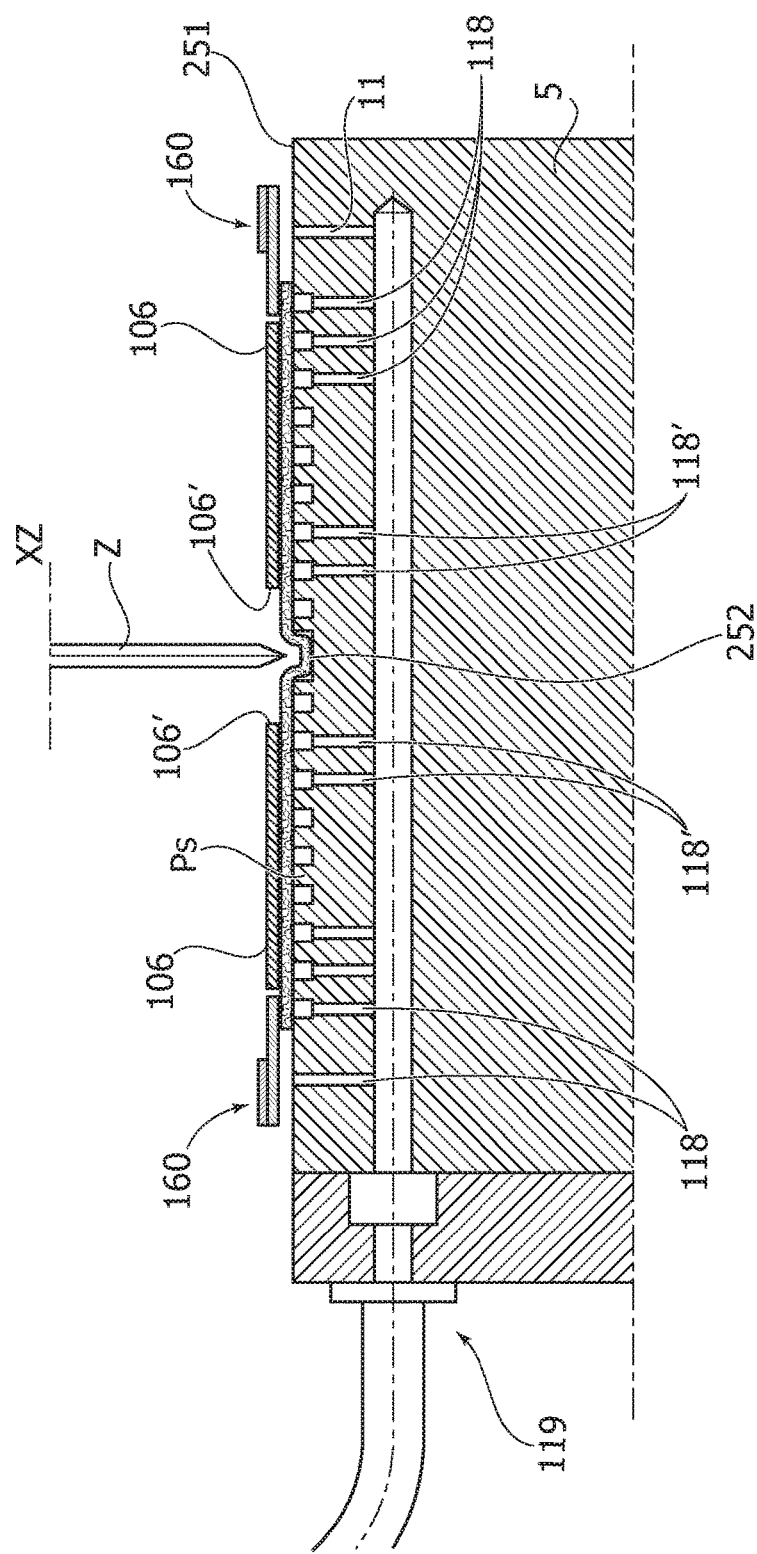
FIG. 15 illustrates a possible variant of the method of producing the material.

In particular, FIG. 15 refers to a solution in which once the web of elastomeric material 106 has been coupled to the first web material 102, it is held in the extended condition not only by the suction holes 118 placed in the vicinity of its longitudinal edges, but also thanks to further anchorage means 118' (which, in this case as well, can advantageously be suction holes connected to the sub-atmospheric pressure source 80 with appropriate vacuum distribution means 119), which typically perform two linear patterns of holes 118' placed laterally to the longitudinal axis of the web of elastomeric material 106, in a more internal position with respect to the suction holes 118, with a central longitudinal region devoid of anchoring means, which can have a width in the order of 1-2 cm. In these conditions, the web of elastomeric material 106 is cut along its longitudinal axis so as to form two portions of elastomeric web material 106 parallel to each other.

The longitudinal cutting operation of the web of elastomeric material 106 can be carried out, for example, by means of a knife Z rotating around an axis XZ exploiting the fact that, at the cutting point, the first web material 102 tends to automatically form a kind of cleft. This is because on the outer surface 251 of the roller 25, an annular groove 252 is typically formed in which said first web material 102 is wedged, forming a wrinkle that is not affected by the action of cutting.

The cutting operation, conducted when the web of elastomeric material 106 is maintained in the transversely extended form, means that the portions of this web comprised between the anchorage means 118' and the cutting line, and which are located on the central longitudinal region of the roller 25 devoid of anchoring means, can retract, consequently forming two tails 106' of extensible elastomeric material that are no longer extended.

Once the longitudinal cutting of the elastomeric material web 106 has been carried out, coupling is performed of the second web material 104 to the first web material 102, interposing between them the two parallel web portions of elastomeric material 106 and the connection formations 160 between them. Subsequently, the sandwich structure thus composed can be subjected to the welding process and to any other folding processes 40 and reinforcing pressing 45 of the connection formations 160.

The result that follows is the formation of webs of composite material 100', 1008', 1009' illustrated in FIGS. 16 and 17, which have a structure essentially similar to that of the webs 100, 1008, 1009 described above, but with a central region 1005' and, respectively, proximal regions 1062, not elasticized.

In a further embodiment illustrated in FIG. 18, the production of a transversely extensible elastic laminar web material 100" provided with connection formations 160 can be implemented by applying one or more webs of elastomeric material 106 between the first and the second web materials 102 and 104 in the transversely relaxed conditions (i.e. not transversely extended). In said embodiment, therefore, the elastic material 106 is not stretched transversely by the spreading-apart device 126, which is typically replaced by a simple cylindrical roller.

Therefore, in the aforesaid further embodiment, the transversely extensible elastic laminar web material 100" comprising the web of elastomeric material 106 in a relaxed condition and the plurality of connection formations 160 interposed between the first and the second web materials 102 and 104, after having been subjected to the welding treatment but before being directed to the folding 40 and pressing 45 devices of the connection formations 160 already described above, can be made transversely extensible by causing it to flow through an activation device of the elastic material, which lengthens the elastomeric web material 106 in the transverse direction Y, permanently deforming the first and the second web materials 102 and 104.

An activation device of the elastic material advantageously applicable in the preferred embodiment can be the activation apparatus of the elastic material described in the document EP 1 982 823 B1 entitled "Method and device for treating web material" owned by the applicant.

Each transversely extensible elastic laminar web material 100, 100' and 100" thus obtained can be wound into rolls, then the rolls thus formed can be directed towards a utilization process, proceeding, if necessary, to their separation (i.e. to the longitudinal cutting of the sandwich 100, 100' and 100" as exemplified in FIG. 10, to form webs 1008, 1008', 1009, 1009') only at a later step of the manufacturing process of the disposable absorbent product, for example in the moment in which the two webs 1008, 1008', 1009, 1009' are produced as they are intended to form elastic side panels located on opposite sides of the same sanitary product 10.

Of course, without prejudice to the principle of the invention, the details of construction and the embodiments can be varied, even significantly, with respect to those illustrated here, purely by way of non-limiting example, without departing from the scope of the invention as defined by the attached claims. This applies in particular, but not exclusively, to the possibility—already mentioned above—to use different materials for the purposes of producing the sandwich 102, 104, 160 and 106, from those to which reference was previously made by way of example. For example, one or both layers 102 and 104 may be constituted, instead of a non-woven fabric, by a film of plastic material such as polythene. As a further example, the elastic material could be a polyurethane foam that, by already being a breathable material per se, further increase the breathability of the side panels 16.

The invention claimed is:

1. A method for producing a transversely extensible elastic laminar web material comprising the steps of:
    feeding a first web material permeable to gases having a first and a second distal region adjacent to respective longitudinal side edges and a central region between said distal regions;
    placing the first web material on an outer surface of a cylindrical roller, rotating around its own horizontal axis;
    retaining said first and second distal regions on the outer surface of said roller and keeping said first web material in an extended condition by a plurality of suction holes and a vacuum distribution system, which connect the outer surface of the roller with a sub-atmospheric pressure source;
    feeding a plurality of connection formations;
    applying said plurality of connection formations to at least one of said first and second distal regions of said first web material, said connection formations protruding from said respective longitudinal side edge of said first web material;
    holding in position on the roller said plurality of connection formations by said suction holes connected to said sub-atmospheric pressure source by said vacuum distribution system;
    feeding a web of elastomeric material;
    coupling said web of elastomeric material to said first web material at said central region of said first web material;
    holding in position and making to adhere said web of elastomeric material to the first web material by said suction holes connected to the sub-atmospheric pressure source by said vacuum distribution system;
    feeding a second web material having a first and a second distal region adjacent to the respective longitudinal side edges and a central region between said distal regions;
    coupling said second web material to said first web material with said elastomeric web material and said plurality of connection formations interposed between them; and
    joining said elastomeric web material and said plurality of connection formations to said first and second web materials with mechanical welds.

2. A method according to claim 1, wherein said elastomeric web material is fed and maintained in a transversely extended condition.

3. A method according to claim 2, wherein said elastomeric web material is cut longitudinally so as to form two parallel portions of said elastomeric web material having inner edges facing each other and free to partially retract towards the respective longitudinal side edges of said first web material, before said step of coupling said second web material to said first web material.

4. A method according to claim 1, wherein said welds create an array of openings in said elastomeric web material that confer characteristics of permeability to gases to said elastomeric web material.

5. A method according to claim 1, further comprising applying said plurality of connection formations to each of the distal regions of said first web material at a constant spacing pitch.

6. A method according to claim 5, wherein said connection formations are applied to said first and second distal regions of said first web material juxtaposed to each other.

7. A method according to claim 6, wherein said connection formations are applied to said first and second distal regions of said first web material offset from each other.

8. A method according to claim 5, comprising the additional step of longitudinally cutting said transversely extensible elastic laminar web material.

* * * * *